United States Patent [19]

Wallach

[11] Patent Number: 4,944,734

[45] Date of Patent: Jul. 31, 1990

[54] BIODEGRADABLE INCONTINENCE DEVICE WITH EMBEDDED GRANULES

[75] Inventor: Donald F. H. Wallach, Brookline, Mass.

[73] Assignee: Micro Vesicular Systems, Inc., Nashua, N.H.

[21] Appl. No.: 371,210

[22] Filed: Jun. 26, 1989

Related U.S. Application Data

[63] Continuation-in-part of Ser. No. 320,944, Mar. 9, 1989.

[51] Int. Cl.⁵ .............................................. A61F 13/16
[52] U.S. Cl. ...................................... 604/358; 604/364
[58] Field of Search ............... 502/404; 604/364, 358, 604/265, 287, 288

[56] References Cited

U.S. PATENT DOCUMENTS

| | | | |
|---|---|---|---|
| 3,777,759 | 12/1973 | Dehmke et al. | 604/370 |
| 3,969,280 | 7/1976 | Sayce et al. | 252/522 |
| 4,002,171 | 1/1977 | Taft | 604/364 |
| 4,009,313 | 2/1977 | Crawford et al. | 604/368 |
| 4,090,013 | 5/1978 | Gamslaw et al. | 526/15 |
| 4,160,063 | 7/1979 | Titus | 428/389 |
| 4,486,335 | 12/1984 | Majewicz | 252/315.3 |
| 4,826,880 | 5/1989 | Lesniak et al. | 521/53 |

FOREIGN PATENT DOCUMENTS

| | | |
|---|---|---|
| 0212969 | 8/1984 | German Democratic Rep. |
| 60-021953 | 2/1985 | Japan |
| 62-112654 | 5/1987 | Japan |

*Primary Examiner*—Jerome L. Kruter
*Attorney, Agent, or Firm*—Lahive & Cockfield

[57] ABSTRACT

The present invention concerns a biodegradable incontinence device such as a diaper. The incontinence device has biodegradability enhancer granules containing an enzyme such as cellulase or hemicellulase embedded therein. The outer layers of the device are preferably made of a biodegradable material such as treated paper or rayon.

20 Claims, 1 Drawing Sheet

BIODEGRADABLE INCONTINENCE DEVICE WITH EMBEDDED GRANULES

REFERENCE TO RELATED APPLICATIONS

This application is a continuation-in-part of U.S. Pat. Application Ser. No. 320,944, filed Mar. 9, 1989, entitled "Biodegradable Superabsorbing Sponge," the disclosure of which is incorporated herein by reference.

BACKGROUND OF THE INVENTION

The present invention relates to incontinence devices such as diapers. More particularly, the incontinence devices disclosed herein are partially, or completely, biodegradable, thereby solving what is probably the major problem in the disposable diaper business today.

Disposable diapers and other disposable incontinence devices have become the norm rather than the exception in the last few years. The breakthrough which lead to the boom in the use of these disposables was the discovery of the polyacrylate "superabsorbers." These superabsorbers absorb many times their own weight in liquids such as urine and saline so that thin diapers could hold an increased amount of water before leaking the fluid back out of the diaper. Leaking back is a problem with infants because of diaper rash and other related wetness problems, and is an even more important problem, in part because of the embarrassment it causes, in those who use incontinence devices, e.g., the elderly. The superabsorbers make the cellulose batt (the thick mat cellulose of fibers in the diaper) much more efficient at trapping liquids, minimizing this problem.

The polyacrylate superabsorbers do have one problem, however; they are not biodegradable. In addition, most diapers today use a polypropylene inner web and a polyethylene outer layer. These plastic webs are also not biodegradable. Therefore, although the cellulosic batt is degradable, the diaper as a whole is not biodegradable. As more and more of these disposable diapers and other incontinence devices are utilized, disposal of these devices becomes an every increasing problem.

Because of the problems associated with the non-biodegradable components of diapers, several alternatives to improve biodegradability have been proposed. For example, it has been suggested that the polypropylene inner layer and polyethylene outer layer be replaced, in certain instances, with polystyrene. Although polystyrene is also not degradable, it purportedly makes a "cleaner" landfill when broken down into small pieces. However, in the normal processing of landfill, the polystyrene will not be broken down and, therefore, yields no improved biodegradability. A second alternative which has been proposed is to use a photosensitive plastic which breaks down slowly upon exposure to sunlight. Although this type of outer plastic layer could improve biodegradability under the proper circumstances, in most instances the diapers are almost immediately covered over as part of landfill so the plastic is not subject to photodegradation.

The problem of disposal of these diapers has gotten so acute that recycling uses, e.g., making the diapers into concrete and/or cardboard, have been suggested. However, since many of the diapers will contain fecal matter, it is unlikely that this type of recycling will be carried out.

Accordingly, an object of the invention is to provide an incontinence device with increased and rapid biodegradability.

A further object of the invention is to provide a diaper or other incontinence device which is completely and rapidly biodegradable.

A still further object of the invention is to provide a diaper containing a superabsorber which is biodegradable.

These and other objects and features of the invention will be apparent from the following description and the drawing.

BRIEF DESCRIPTION OF THE DRAWING

The sole figure of the drawing is a cutaway cross-section of an incontinence device of the invention.

DEFINITIONS

Figure 1:
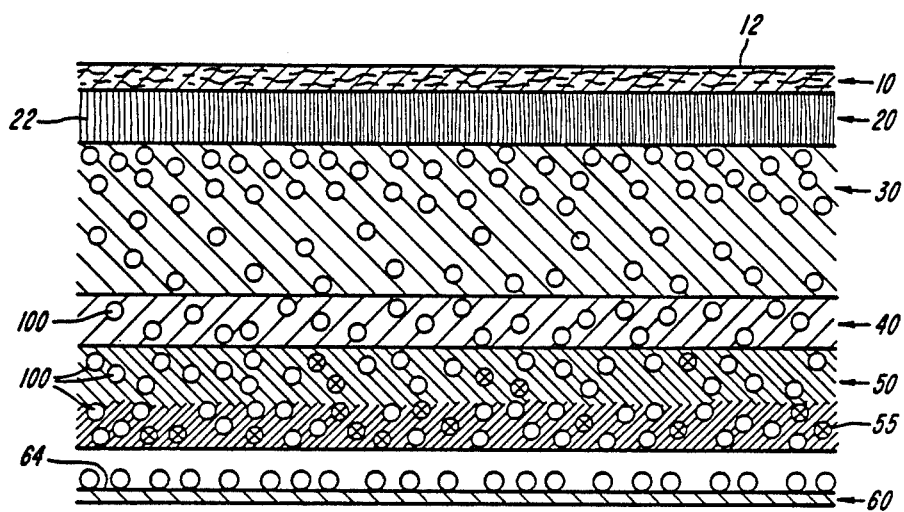

The following definition of terms will assist in understanding the invention:

The term "non-hydrated" means and implies prehydration states, dehydration states, lyophilized states, and any other related state which is lacking water.

The term "substantially hydrophobic region" means and implies a region with a substantial hydrocarbon chain and ring structure.

The term "biodegradability" as used herein means and implies the ability to be broken down into small chemical subunits which can be utilized in the food chain through naturally acting and/or environmentally safe enzymes, bacteria, and spores.

The term "incontinence device" means and implies geriatric and other devices used to trap natural bodily fluids such as feminine napkins, as well as diapers for use by infants and toddlers.

The term "superabsorber" means and implies any material, including, but not limited to, polyacrylate superabsorbers and biodegradable superabsorbers such as are described in U.S. Pat. Application Ser. No. 320,944, which can absorb many times its own weight in water, saline, urine, or other aqueous fluids.

The term "metallic-organic cross-linking agent" means and implies cross-linking agents having both a metal ion, preferably a multivalent metal ion such as aluminum or chromium, and an organic portion such as acetate or an acetate/palmitate complex.

SUMMARY OF THE INVENTION

The present invention features an incontinence device having improved biodegradability. In its most preferred embodiments, the incontinence device or diaper is totally biodegradable.

The incontinence device of the present invention is, like conventional incontinence devices, a multilayer device. The incontinence device has an inner layer made of a material which is substantially nonwettable, but which is porous to allow the transfer of an aqueous solution such as saline or urine into the device. While materials such as polypropylene webs can be used, they are not preferred because of their non-biodegradability. Most preferable, the inner layer is a biodegradable material such as one selected from the group consisting of non-woven cellulosic material, high tensile strength perforated paper, non-woven rayon, and loosely woven rayon. The biodegradable material should be porous but may be treated to make the fibers nonwettable. Treatments which make fibers of this type of material nonwettable include coating the fibers with silicone, lower alkyl silicone halide treatment, or coating with insoluble fatty acids. The inner layer is by convention the layer worn is closest to the skin.

The outer layer is at the opposite extreme of the device. The type of materials which are preferred for use in this outer layer are similar to those used in the inner layer except the outer layer should not be porous to the passage of water, except it may be porous to water vapor. While a polyethylene sheet such as is presently used in diapers could be used, it is not preferred because of its lack of biodegradability. If a non-biodegradable material is used, it may be treated with a superabsorber to improve the efficiency of the incontinence device.

Between the inner and outer layers are one or more absorptive layers formed primarily of the cellulosic materials such as wood pulp. This cellulosic material or batt is similar to that used in conventional diapers except it has biodegradability enhancer granules embedded therein. The biodegradable enhancer granules consist of particulate material such as a capsule, flake, perforated sheet, or other particulate which degrades over time encapsulating a biodegradability enhancer agent. The biodegradability enhancer agent is selected from the group consisting of cellulase, hemicellulase, and/or related cellulose degrading enzymes, and bacteria or spores which release cellulase, hemicellulase, and/or related cellulose degrading enzymes. The preferred capsules for the enhancer granules are formed of a biodegradable synthetic sponge composition which absorbs water and releases the biodegradability enhancer agent after absorption of the water. The preferred synthetic sponge composition is a non-hydrated material formed of a carboxylic acid which has a substantial hydrophobic region and a cellulosic carbohydrate. The synthetic sponge composition can be hydrated and cross-linked simultaneously in the presence of water. The synthetic sponge composition may include a separate cross-linking agent, such as an organo-metallic cross-linking agent which includes a multivalent metal ion. In certain instances, the metallo-organic cross-linking agent can comprises both the carboxylic acid and the cross-linking agent. Other carboxylic acids useful in the synthetic sponge composition are fatty acids such as acetic acid, lauric acid, palmitic acid, stearic acid, oleic acid, benzoic acid, and mixtures and derivatives thereof. The carbohydrate is preferably selected from the group consisting of carboxymethylcellulose, cellulosic gums, and their derivatives and chemical analogues. The synthetic sponge material in the enhancer granules acts, in part, as a superabsorber, retaining many times its weight in hydrating fluids such as saline or urine. In certain instances, the granules can be replaced with a perforated sheet containing the enzymes and spores, or they may be bound to a fiber.

In addition to the biodegradability enhancer granules, the absorptive layer may also include an additional superabsorber. Preferably, the superabsorber is of the same, or a similar, composition as the synthetic sponge used in biodegradability enhancer granules. This superabsorber may be in the form of granules, a sheet, or a non-woven. If a non-woven layer is used on the inside of the outer layer, the non-woven format in the absorptive layer is preferred.

The most preferred structure for the incontinence device has a wicking layer between the inner layer and the absorptive layers. If the inner layer is made of a non-woven, the majority of the fibers will be in a planar direction, parallel in direction to the inner layer surface. The wicking layer has fibers which are preferably at right angles to the inner layer, thereby wicking the liquid away from the inner layer into the absorptive layers along the fibers.

Multiple absorptive layers rather than a single layer are preferred, with a density gradient of cellulose batt such that the loosest packed absorptive layers are closest to the inner layer while the most densely packed are closer to the outer layer. Any superabsorber which is used in addition to the enhanced biodegradable granules will normally be concentrated in the densest layers. In addition, the biodegradability granules will normally also be concentrated in the denser layers where they are most needed.

The following description and the drawing will more clearly illustrate the invention.

DETAILED DESCRIPTION OF THE INVENTION

The present invention features an incontinence device or diaper which is, in its most preferred form, completely biodegradable. This diaper can ameliorate the problems associated with disposability of non-biogradable incontinence devices.

The sole figure of the drawing illustrates a cross-section of a preferred diaper of the invention. The topmost layer 10 is the inner layer of the diaper. Preferably, inner layer 10 is made of a perforated paper or a rayon-type material in either non-woven or loosely woven, e.g., stocking-like, form. This layer is porous, having pores 12 to allow the entry of bodily fluids into the diaper. Another possible material for inner layer 10 is a cellulosic non-woven, preferably with a relative excess of long fibers on the outer face and an excess of short fibers on the inner face. This will also lead water into the diaper. In addition, other thin, porous biodegradable materials could be used for inner layer 10.

However, all of the materials for inner layer 10 should be made hydrophobic. There are a number of different ways this could be done. For example, a solventless silicone treatment such as described in "Surface-applied chemical development," Moore et al., Paper (London) 204 (3):22-23 (1985), or aqueous polysiloxane emulsions or other related systems could provide a silicone treatment. In addition, treatment with a lower alkyl silicone halide such as methyltrichlorosilane could be used. U.S. Pat. No. 4,339,479, issued on application of Rodbart, describes a method of using these silicone halides for making Kraft paper nonwettable. Further, coating or impregnation of inner layer 10 with an insoluble fatty acid, e.g., aluminum stearate or aluminum palmitate, could make the layer hydrophobic. This type of inner layer would be preferable to the standard polypropylene layer currently used in diapers since polypropylene is not biodegradable.

Layer 20 is the optional wicking layer. Wicking layer 20 is preferable cellulosic, e.g., wood pulp, arranged with preferred fiber orientation at right angles to inner layer 10. The purpose of this layer is to allow liquids to wick, either inside the fibers or along the outside of the fibers, from inner layer 10 to first absorptive layer 30. The fibers 22 have biodegradability granules 100 interdispersed therethrough. These granules, which are described in more detail below, contain an enzyme such as cellulase, hemicellulase, or a related cellulose degrading enzyme, or a bacteria or spore which secretes one of these enzymes. For example, see "Synthesis and secretion of heat-stable carboxymethylcellulase from *Clostridium* thermocellum in *Bacillus* subtilis and *Bacillus* starothermophilus," Soutschek-Bauer and Staudenbauer, Mol.Gen.Genet. 208(3):537–541 (1987). These granules release the cellulase, hemicellulase or other related cellulose degrading enzymes which break down the cellulose fibers in the absorptive batt, as well as the carboxymethylcellulose in the absorptive capsules themselves, upon hydration and warming. Spores capable of being used are sold as compost accelerators, assisting in the breakdown of plant waste into usable components. The spores normally sporulate within minutes of hydration.

First absorptive layer 30 is contiguous with wicking layer 20. Typically, layer 30 is a highly porous cellulosic batt such as is currently being used in many diapers. The difference between this layer and that used in the present diapers is the presence of the biodegradability granules 100. This layer has a much greater wettability then either inner layer 10 or wicking layer 20.

Contiguous with the first absorptive layer 30 is second absorptive layer 40. Again, this layer 40 is a cellulosic batt but it is more compact and has smaller pore size than that of the first absorptive layer 30. Because of this increase in fiber density, it can hold more liquid than layer 30. Again, this type of layer is conventional in diapers except for the presence of biodegradability granules 100.

Third absorptive layer 50 is another cellulose batt layer but it is still more compacted than first or second absorptive layers 30 and 40. In addition to the cellulosic fibers, this layer includes biodegradability granules 100 in a higher concentration to match the higher concentration of cellulose batt fibers, as well as a superabsorber 55. Layers like this layer 50 made of highly compacted cellulosic fiber have been used in diapers in the past with a superabsorber 55 dispersed therein but only non-biodegradable polyacrylate superabsorbers have been used. In the preferred versions of the present invention, a biodegradable superabsorber, in granular, sheet, or non-woven form, is used.

Outer layer 60, which encloses the diaper, is made of similar materials as inner layer 10 except it may include biodegradability granules 100 on the inner surface 64 and, in some embodiments, have a non-woven superabsorber on inner surface 64. This non-woven can be achieved by dipping surface 64 into a solution which will form a non-woven and letting it dry. Such a dipping step and material is described below.

The preferred biodegradable superabsorbers for use in the present invention are those described in U.S. Pat. Application Ser. No. 320,944. These superabsorbers can be made in granular, sheet, or non-woven form. Methods of preparation of various forms of this type of superabsorber are described in the following non-limiting Examples

EXAMPLE 1.

In this Example, a granular form of a superabsorber particularly useful for practice of the invention is described.

One mole of aluminum isopropoxide in mineral spirits is mixed with 2 moles glacial acetic acid for 1 hour at 50° C. until reacted. After reaction, carboxymethylcellulose (CMC) containing one mole percent palmitic acid (based on CMC) is added in a ratio of four moles CMC/mole aluminum. The reaction is allowed to continue for 6 hours. The resulting CMC/aluminum acetate/palmitate complex is then air dried into discrete granules. The reaction is more than 80% complete. The saline uptake characteristics of these granules are comparable with presently used polyacrylate superabsorbers.

EXAMPLES 2.

To make perforated sheets, biodegradability enhancer granules, or non-woven sheets of the superabsorber, a metallo-organic cross-linking agent or complex is first made. A preferred metallo-organic complex is a palmitate-based aluminum complex. Approximately 0.64 g of palmitic acid (0.25 mmol) is dissolved in 5 ml of ethanol with 1.4 g (10 mmol) of aluminum monoacetate stabilized with boric acid in 5 ml of water. The resulting opalescent suspension contains the metallo-organic cross-linking agent.

A preferred sponge-like material for use in the invention is made by mixing approximately 0.2 g of carboxymethylcellulose, 0.004 g of palmitic acid and 0.2 ml of the metallo-organic cross-linking agent in saline. This material, is dried as a perforated sheet useful as a superabsorber in the absorptive layers of the diaper of the present invention.

EXAMPLE 3.

In this Example, the biodegradability enhancer granules are made using the same sponge-like material described in Example 2.

Powdered P. funiculosum cellulase (Sigma Chemical Co., St. Louis, Mo.) is dispersed into the sponge-forming material which is then formed into droplets in 50% isopropanol. These droplets, when dried, form the enhancer granules, encapsulating the cellulase in the superabsorber. The cellulase can be replaced by hemicellulase and other related cellulase degrading enzymes, or bacteria or spores which release cellulose degrading enzymes. These enhancer granules, as well as granulated superabsorber, can be put into the cellulosic batt during the fluffing procedure, replacing the superabsorbant now used.

EXAMPLE 4.

This Example illustrates how to make a non-woven superabsorber useful in the invention. The same superabsorber solution is made as in Examples 2 and 3. The superabsorber is dissolved in 0.5–1.0 M sodium hydroxide and placed in a standard spinnerette apparatus such as is used to made rayon fibers. This spinnerette apparatus shoots the liquid superabsorber-sodium hydroxide solution into a vat of isopropanol containing a matching amount (0.5–1.0 M) acetic acid, thereby forming fibers. The fibers are matted into a non-woven and dried. These non-woven fibers can be placed into the cellulose batt, acting as a superabsorber.

Further details of the procedures for making the superabsorbers and further materials which may be used as superabsorbers are described in U.S. Pat. Application Ser. No. 320,944.

In some instances, it is preferable to have some superabsorber attached directly onto surface 64 of outer layer 60. If granulated superabsorber is used, it can be glued directly to inner surface 64. If a non-woven is preferred, surface 64 is dipped into a vat of preformed liquid superabsorber and then allowing it to dry as a perforated sheet.

Not all of the biodegradable layers described herein need be used to provide enhanced biodegradability as compared with present incontinence devices. However, since the presently biodegradable portions of these devices, e.g., the cellulose batt, is surrounded by a nondegradable outer shell, and further, since in terms of biodegradability the outer shell is dominant, some form of biodegradable outer shell is preferable. In any case, the use of the biodegradability enhancer granules will provide better biodegradability then is presently available.

The foregoing description is illustrative only and those skilled in the art may find other materials and methods which may accomplish the same results. Such other materials and methods are included within the following claims.

What is claimed is:

1. An incontinence device having improved biodegradability comprising:
   an inner layer which is substantially porous to allow the transfer of an aqueous solution into said device, said inner layer being made of a material which is substantially nonwettable;
   one or more absorptive layers formed primarily of a cellulosic material, said cellulosic material having biodegradability enhancer granules embedded therein, said enhancer granules containing of a particulate material which degrades over time encapsulating a biodegradability enhancer agent selected from the group consisting of cellulase, hemicellulase or related cellulose degrading enzymes, and bacteria or spores which release cellulase, hemicellulase or related cellulose degrading enzymes; and
   an outer layer which is substantially impermeable to water.

2. The incontinence device of claim 1 wherein said capsule of said enhancer granules comprises a biodegradable synthetic sponge composition which absorbs water and releases said biodegradability enhancer agent from said granules after said absorption of water.

3. The incontinence device of claim 2 wherein said synthetic sponge composition comprises a non-hydrated material which includes a carboxylic acid with a substantial hydrophobic region and a cellulosic carbohydrate, which material is capable of being hydrated and cross-linked simultaneously in the presence of the water.

4. The incontinence device of claim 3 wherein said synthetic sponge composition further comprises a cross-linking agent.

5. The incontinence device of claim 4 wherein said cross-linking agent comprises a metallo-organic cross-linking agent which includes a multivalent metal ion.

6. The incontinence device of claim 5 wherein said metallo-organic cross-linking agent comprises both said carboxylic acid and said cross-linking agent.

7. The incontinence device of claim 3 wherein said carboxylic acid comprises a fatty acid.

8. The incontinence device of claim 7 wherein said fatty acid is selected from the group consisting of acetic acid, lauric acid, palmitic acid, stearic acid, oleic acid, benzoic acid, and mixtures and derivatives thereof.

9. The incontinence device of claim 3 wherein said cellulosic carbohydrate is selected from the group consisting of carboxymethylcellulose, cellulosic gums, and their derivatives and chemical analogues.

10. The incontinence device of claim 3 wherein said absorptive layer further comprises a superabsorber composition.

11. The continence device of claim 10 wherein said superabsorber composition comprises said synthetic sponge composition, or a derivative or chemical analog thereof.

12. The incontinence device of claim 1 wherein said absorptive layer comprises a plurality of absorptive layers with increasing density in the packing of said cellulosic material at the portion closest to said outer layer.

13. The incontinence device of claim 1 wherein said inner layer comprises a biodegradable material.

14. The incontinence device of claim 13 wherein said biodegradable material is selected from the group consisting of non-woven cellulosic material, high tensile strength perforated paper, non-woven rayon, and loosely woven rayon, said biodegradable material being treated to make the fibers nonwettable.

15. The incontinence device of claim 14 wherein said biodegradable material is treated with a material selected from the group consisting of silicone, lower alkyl silicone halide, and insoluble fatty acids to make the fibers nonwettable.

16. The incontinence device of claim 1 wherein said outer layer comprises a biodegradable material.

17. The incontinence device of claim 16 wherein said biodegradable material is selected from the group consisting of non-woven cellulosic material, high tensile strength perforated paper, non-woven rayon, and loosely woven rayon, said biodegradable material being treated to make the fibers nonwettable.

18. The incontinence device of claim 17 wherein said biodegradable material is treated with a material selected from the group consisting of silicone, lower alkyl silicone halide, and insoluble fatty acids to make the fibers nonwettable.

19. The incontinence device of claim 1 further comprising a wicking layer between said dinner layer and said absorptive layer.

20. The incontinence device of claim 1 wherein said device comprises a diaper.

* * * * *